(12) United States Patent
Albert

(10) Patent No.: US 6,476,385 B1
(45) Date of Patent: Nov. 5, 2002

(54) CLEANING MANAGEMENT KIT AND METHOD OF USE

(76) Inventor: Peter M. Albert, 937 Beaver Bank Cir., Baltimore, MD (US) 21286

(*) Notice: Subject to any disclaimer, the term of this patent is extended or adjusted under 35 U.S.C. 154(b) by 0 days.

(21) Appl. No.: 09/531,540

(22) Filed: Mar. 20, 2000

Related U.S. Application Data

(60) Provisional application No. 60/125,512, filed on Mar. 22, 1999.

(51) Int. Cl.$^7$ ................................................. G01N 21/64
(52) U.S. Cl. ...................................... 250/302; 250/301
(58) Field of Search ................................. 250/302, 301

(56) References Cited

U.S. PATENT DOCUMENTS

| | | | | | |
|---|---|---|---|---|---|
| 2,600,221 A | * | 6/1952 | Domingo | ..................... | 134/18 |
| 4,621,193 A | * | 11/1986 | Van Hoye | ................... | 250/302 |
| 5,225,675 A | * | 7/1993 | O'Donnell | ................. | 250/302 |
| 5,804,822 A | * | 9/1998 | Brass et al. | ................ | 250/302 |

OTHER PUBLICATIONS

Tracer–Tech. Datasheet. Uresco, Inc., 1965.*

* cited by examiner

Primary Examiner—Constantine Hannaher
(74) Attorney, Agent, or Firm—Law Offices of Royal W. Craig

(57) ABSTRACT

A cleaning inspection kit inclusive of various compositions of water-soluble invisible fluorescent ink and various applicators therefor which are suited for a number of different surfaces, and a hand-held ultra-violet light. The appropriate applicator is used to mark an area with invisible compound prior to cleaning. After the area has been cleaned an inspection is made with the ultra violet light to expose the original area and to determine whether remnants of the original mark are still there. If so, the area could not have been properly cleaned. However, if the original mark is gone then the area was cleaned. The system allows management to inspect the quality of cleaning and maintenance services. The kit is simple to use as the inks are applied by convenient pen, powder or spray applicators, and a portable ultra-violet light is provided for fluorescing the inks. The method is non-destructive as all of the ink compositions wash away upon normal cleaning.

2 Claims, 5 Drawing Sheets

Dirty

CLEANING MANAGEMENT KIT AND METHOD OF USE

CROSS-REFERENCE TO RELATED APPLICATIONS

The present application derives priority from U.S. Provisional Application Ser. No. 60/125,512 for "CLEANING MANAGEMENT KIT AND METHOD OF USE"; filed: Mar. 22, 1999.

BACKGROUND OF THE INVENTION

1. Field of the Invention

The present invention relates to systems for ensuring the quality of cleaning and maintenance services and, more particularly, to an inspection method and device.

2. Description of the Background

It is known that certain compounds are highly reflective of ultra-violet radiation, and this principle has been used to make certain dyes that are transparent in white light, yet luminous in ultra-violet light. For example, U.S. Pat. No. 3,589,280 to Wilde shows a device for coding containers by marking with normally transparent and invisible indicia. The containers are marked with ultraviolet ink that is normally invisible, but which becomes visible upon UV illumination.

This and other known verification/authentication applications require highly specific inks designed to adhere to the particular paper or article to be imprinted and to fluoresce at a particular wavelength. In most of these authentication applications it has also been necessary to employ specialized lighting to illuminate the ink. Such requirements are driven by the need to deter counterfeiters, and they result in relatively expensive authentication systems. Nevertheless, the cost is justified in light of the inherent value of the items being authenticated, e.g., currency.

Fluorescent inks have been used in other contexts, namely for artistic and novelty items. For instance, U.S. Pat. No. 5,698,614 to Uedae et al. shows an oil-based fluorescent ink composition which comprises propylene glycol monomethyl ether as a solvent a solution type fluorescent pigment dissolved in the organic solvent, and a ketone resin.

Likewise, ultra-violet lights have been used in other applications. For instance, U.S. Pat. No. 5,572,319 discloses a stain detector apparatus and method for detecting stains in a fabric using an incandescent lamp and a fluorescent lamp for projecting light rays toward the fabric.

Despite the above, many utilitarian applications for the concept have gone largely unnoticed because they are not justified by the expense in developing the proper inks and lighting. One particular application is in cleaning management and inspection. Various systems have been used as a quality assurance measure in the cleaning services industry. For example, electronic check points are now in wide use, and these require a cleaning person to register themselves using an electronic key, magnetic card reader or the like, at each station to be cleaned. While such approaches generally track the presence and progress of the cleaning person about their rounds, they fail to check the actual quality of the cleaning effort.

It would be greatly advantageous to make use of the properties of invisible fluorescent ink to provide a quality assurance measure for the cleaning industry by which management can ensure that certain areas are being thoroughly cleaned.

SUMMARY OF THE INVENTION

It is, therefore, an object of the present invention to provide a system by which management can ensure the quality of cleaning and maintenance services by physically inspecting whether invisible ink markings have been removed by a cleaning person.

It is another object to provide a variety of water-soluble invisible ink compositions that can be applied to a variety of common surfaces, all of which inks wash away upon normal cleaning.

It is still another object to provide a comprehensive cleaning management kit and method of using the same including economical and convenient applicators for the above-described inks, and economical and convenient illuminators for fluorescing the inks.

It is still another object to provide a cleaning management method for applying information to common surfaces using a special marking ink that contains a fluorescent material which is invisible under normal light but is visible upon being exposed to ultra violet rays, and for inspecting said surfaces using an ultra violet light to ensure that said information has been properly removed by cleaning personnel.

According to the present invention, the above-described and other objects are accomplished by providing various compositions of water-soluble invisible ink and various applicators therefor which are suited for a number of different surfaces. One formula is dispensed from a pen applicator is best suited for applying the ink to hard surfaces such as porcelain, FORMICA® laminate, metal, mirrors, tiles or other impervious surfaces in order to perform cleaning inspections on areas such as bathrooms, kitchens, offices etc. to ensure proper cleaning is being done.

Another formula dispensed from the same pen applicator uses less alcohol and is best suited for application to fabrics such as sheets, linens, drapes, furniture, wall partitions, etc. to ensure proper cleaning. This formula is gentler and ensures that the fabric is not damaged.

Another formula is provided in powder form for application via a roller applicator to carpets to ensure proper vacuuming. Certain plush and/or coated carpets would be better covered by a spray-applicator, and the present invention also provides a spray form and applicator suited for this purpose.

Still another formula is designed for application in wax crayon form to hard floorings or surfaces that might have a surface coating like wax (i.e. VCT, tile, wood or marble floors).

Despite the various compositions and method of application, all of the invisible inks are formulated so that they are not absorbed by the surface or fabric, but instead reside on top and are removed with normal cleaning. These ink compositions have many potential applications including the cleaning kit and method of the present invention. Additionally, the ink compositions in and of themselves are suitable for advertising that needs to be removed, such as nightly meal specials at a restaurants. They also provide an excellent toy to allow children to write secret or special messages that need to be removed, e.g., removable messages on the walls of their room or on clothes with that would only be visible under ultra violet light.

In the context of cleaning inspection according to the present invention, any one or all of these specially-formulated inks are combined in a kit with a convenient hand-held ultra-violet light. An area to be cleaned is marked with the appropriate invisible ink marker prior to cleaning. After the area has been cleaned an inspection is made with a ultra violet light to expose the original area marked and to determine whether the original mark is still there. If so, the area could not have been properly cleaned. However, if the original mark is gone then the area was cleaned.

The above-described system allows management to inspect the quality of cleaning and maintenance services by physically inspecting whether the invisible ink markings have been removed. The kit is simple to use as the inks are applied by convenient pen, powder or spray applicators, and a portable ultra-violet light is provided for fluorescing the inks. So long as the appropriate marking compound and applicator is used for a given surface, the method is completely non-destructive as the marking composition will wash away upon normal cleaning.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

Figure 1:
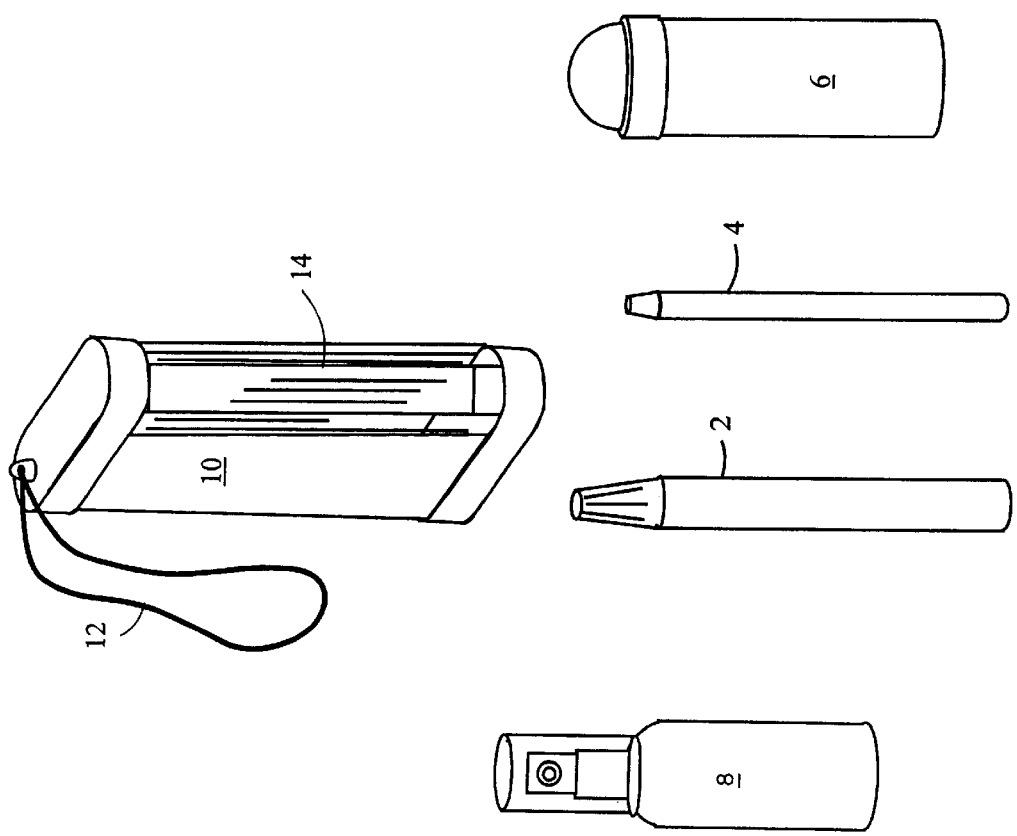
FIG. 1 is a side perspective view of a cleaning management kit including four different types of applicators 2–8 for five different formulas.

FIG. 1 is a side perspective view of a cleaning management kit including three different types of applicators 2–8 for each of the four above-described formulas, one pen applicator 2 for applying one ink formulation to hard surfaces such as porcelain, FORMICA® laminate, metal, mirrors, tiles or other impervious surfaces, and a second ink formulation to fabrics such as sheets, linens, drapes, furniture, wall partitions, etc. to ensure proper laundering. In addition, a third formulation of invisible marking compound is provided for spray-application to thick-pile carpets, hard-coated flooring, or other heavy-textured surfaces, and a conventional atomizer 8 can be used for this purpose. A wax crayon applicator 4 is provided for applying a wax formulation to hard floorings or surfaces that might have a surface coating like wax (i.e. VCT, tile, wood or marble floors). Still another formula of invisible ink is provided in powder form for application via a roller applicator 6 to fabrics, carpets and the like. A variety of suitable roller-applicators are available for other powders and liquids such as antiperspirants.

In addition to the above-described applicators 2–8, an economical and convenient illuminator 10 is provided for fluorescing all three formulas once applied. All of the invisible compositions are formulated so that they are not absorbed by the respective surfaces or fabrics, but instead reside on top and are removed with a simple cleaning.

Figure 2:
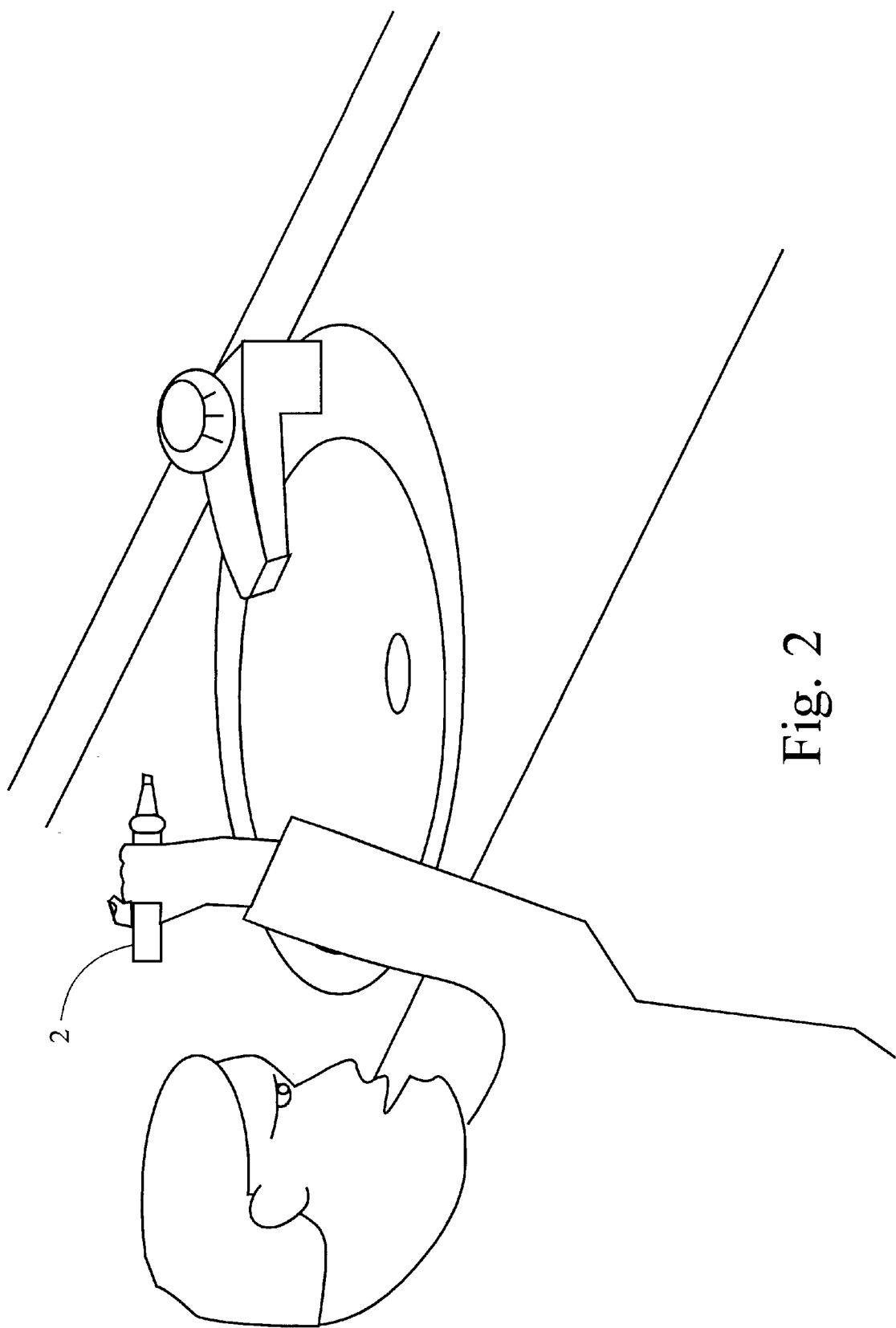
FIG. 2 is a perspective view illustrating the use of the cleaning management kit to mark a sink according to the method of the present invention.

FIG. 2 is a perspective view illustrating the use of the cleaning management kit to inspect a sink according to the method of the present invention. The pen applicator 2 is used for applying the hard-surface ink formulation to all surfaces such as porcelain, FORMICA® laminate, metal, mirrors, tiles or other impervious surfaces. This pen 2 is especially useful in bathrooms as shown. A particular area to be cleaned is marked simply by writing with the appropriate invisible ink marker 2 prior to cleaning. Preferably, the user writes the date of marking. Subsequently, after the area has been cleaned, an inspection can be made with a ultra violet light to determine whether the marking was removed by thorough cleaning procedures.

Figure 3:
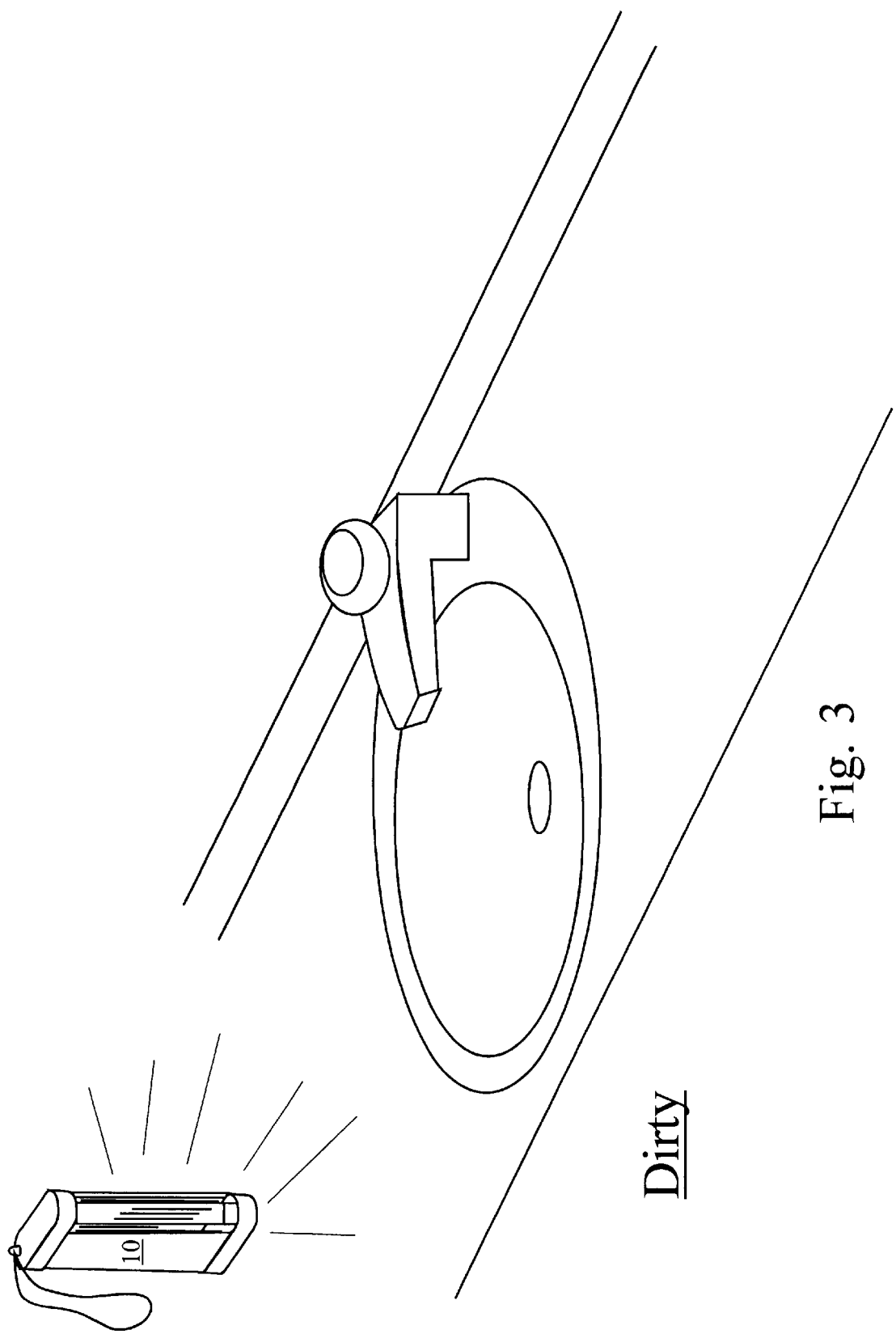
FIG. 3 is a perspective view illustrating a subsequent failed inspection of the sink of FIG. 2.

FIG. 3 is a perspective view illustrating the subsequent inspection method. The user exposes the original area marked with the ultra-violet light 10 to determine whether the original mark is still there. In the illustrated case, the marking reflects the UV light, and it clearly appears after cleaning that the area could not have been properly cleaned.

Figure 4:
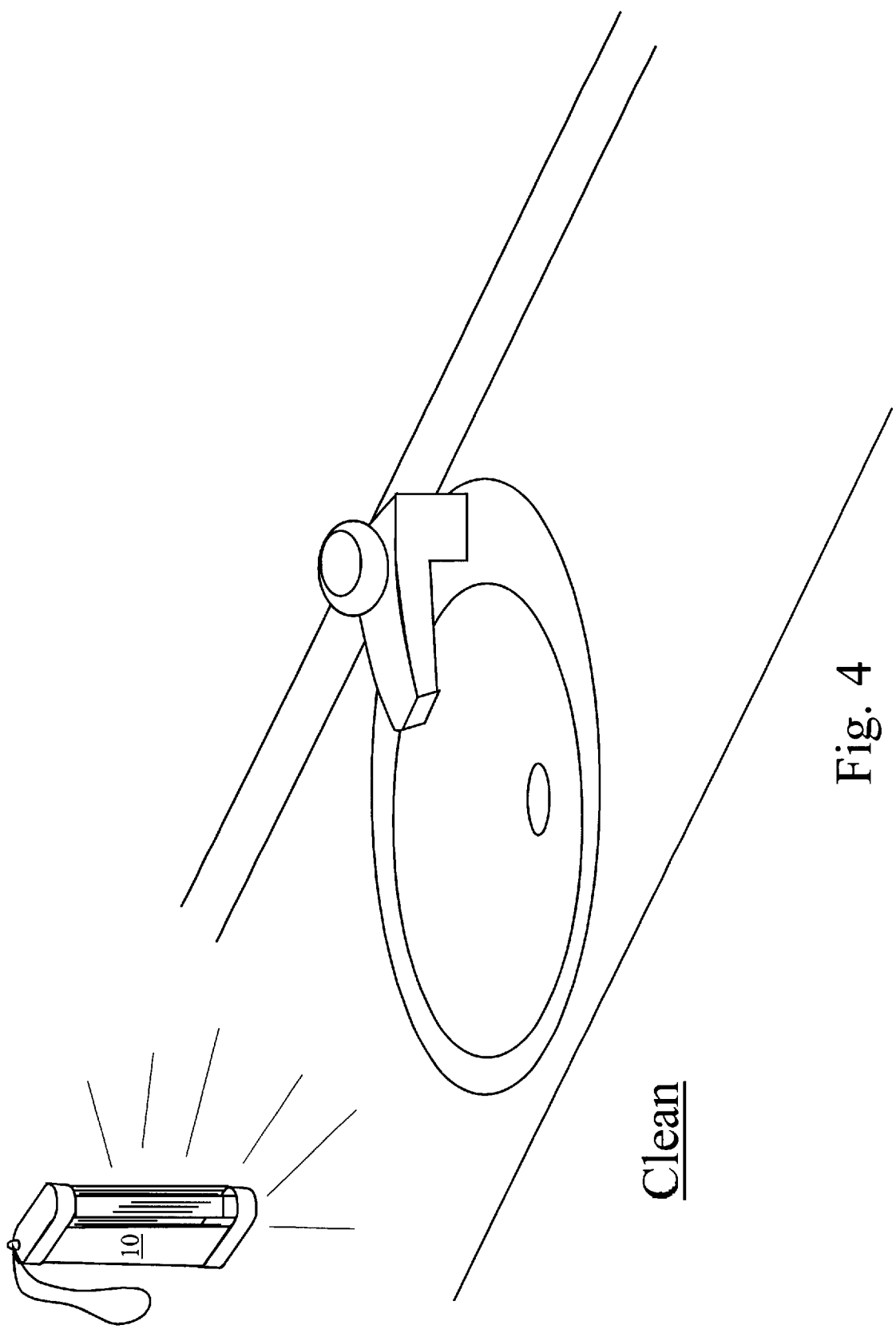
FIG. 4 is a perspective view illustrating a subsequent passed inspection of the sink of FIG. 2.

FIG. 4 is a perspective view illustrating the absence of the marking after cleaning. In this case, the original mark is gone and the area was properly cleaned. Either way, management is able to record and track the result. Over time the kit allows management to periodically inspect and maintain the quality of cleaning and maintenance services. The kit is simple and inexpensive to use as the inks are adaptations of existing formulas and are applied by convenient pen, powder or spray applicators 2–6. The portable ultra-violet light 10 for fluorescing the inks is also simple to use. The method is non-destructive as all of the marker compositions wash away upon normal cleaning.

The hard-surface ink formulation is a water-based ultra-violet ink with the following formulation:

| Ingredient | % (weight) |
| --- | --- |
| Propylene Glycol Methyl Ether | 10 |
| Poly Vinyl Pyrolidone | 5 |
| Hetrocyclic dye | 4 |
| Water | 27 |
| Isopropanol | 54 |

The formulation is completely soluble in water, and it is colorless and odorless. It evaporates slowly and will remain on the surface for extended periods of time. The composition is relatively non-volatile, non-toxic and is completely safe for use in areas such as bathrooms, kitchens, etc. The formulation yields a water-based ink form that can be dispensed from a conventional felt-tipped marker. The ink is readily contained in the capillary or valve reservoir of the plastic cartridge and will not spill under normal conditions.

A second formulation of invisible marker compound and pen applicator provides for the application to fabrics such as sheets, linens, drapes, furniture, wall partitions, etc. to ensure proper cleaning. This formula is essentially the same as described above except that the proportion of water relative to isopropanol is increased to ensure that the fabric is not damaged. As above, this diluted formula yields a water-based ink form that can be dispensed from a felt-tipped marker to fabrics. Preferably, the felt of the marker is selected to be a courser grade in this case to improve the area of contact with the fabric. On the other hand, this makes it somewhat more difficult to saturate the felt and the user should shake well before use, and press down with the tip until it becomes saturated.

A third formulation of invisible marking compound and spray applicator 8 provides for spray-application to thick-pile carpets, hard-coated flooring, or other heavy-textured surfaces. Preferably, a conventional atomizer is used to apply the spray. This formula is substantially the same as the above-described diluted formulation above except that the proportion of water relative to isopropanol is further increased. This is necessary because a greater volume of marker compound is emitted from the atomizer and a diluted concentration protects the carpet.

Still another marker composition is provided in powder form for application via a roller-applicator 6 to carpets. The powder formulation is a water-soluble ultraviolet powder with substantially the following composition:

| Ingredient | % (weight) |
|---|---|
| 2.2 BIS Butylbenzoxazole | 100 |

Again, the formulation is completely soluble in water. It is odorless, non-staining, and it bears a nearly invisible light yellow color. The powder does not evaporate and will remain on the carpet for extended periods of time. The powder is non-volatile, non-toxic and is completely safe for use in all carpeted areas. The powder form can be dispensed from a conventional roller-applicator 6 such as commonly used by powder antiperspirant manufacturers. Example of such applicators are shown in U.S. Pat. No. 4,002,411 and U.S. Pat. No. 5,116,156.

A fourth composition is provided in wax crayon form for application to hard floorings or surfaces that might have a surface coating like wax (i.e. VCT, tile, wood or marble floors). The crayon formula has a wax base, and may include stearic acid as do conventional crayons. In addition, a fluorescent pigment is used which comprises Hetrocyclic dye (approximately 4% by weight). Use of the dye in small amounts enables the fluorescent properties when exposed to ultra-violet light illumination, while still maintaining the required performance qualities of the crayon wax.

Figure 5:
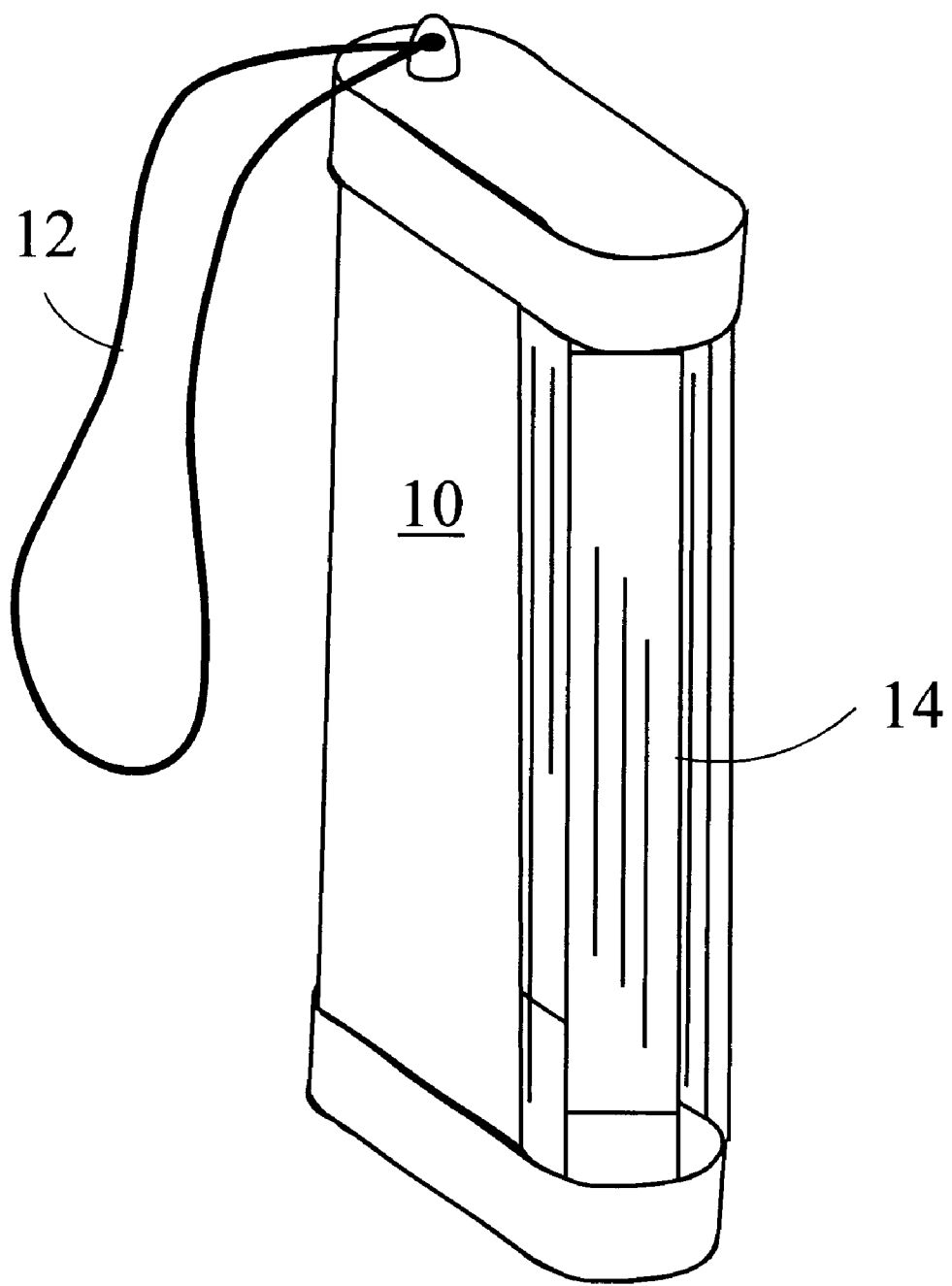
FIG. 5 is a perspective view of a portable ultraviolet fluorescent light 10 according to the present invention.

FIG. 5 is a perspective view of a portable ultraviolet fluorescent light 10 according to the present invention. For greatest convenience, the light 10 is as small as possible. Acceptable products are currently available at only 16.51 cm. (6½") in length and fit easily inside a shirt pocket. Preferably, a lanyard 12 is provided for easy carrying. Any such commercially-available products may be used so long as they are capable of illuminating the fluorescent compositions disclosed above. This basically requires a fluorescent lamp, and an ultraviolet filter around the lamp. It has been found that a 4 watt transistorized ultraviolet bulb 14 operating on four AA batteries (not shown) provides sufficient illumination. A variety of commercially-available lamps are suitable for use as lamp 10, and one such example is shown in U.S. Pat. No. 3,725,694 to D'Amato, issued on Apr. 3, 1973.

In the context of the method of cleaning inspection according to the present invention, one or more of the markers incorporating the specially-formulated inks are combined in a kit with the hand-held ultra-violet light 10. To use the kit, the user marks an area to be cleaned with the appropriate invisible ink marker, crayon, atomizer or roller prior to cleaning. Where possible, the marking should include the date of marking. After the area has been cleaned, an inspection is made with a ultra violet light to expose the original area marked and to determine whether the original mark is still there. If so, the area could not have been properly cleaned. However, if the original mark is gone then the area was cleaned thoroughly.

The above-described system allows management to inspect the quality of cleaning and maintenance services by physically inspecting whether the invisible ink markings have been removed. The kit is simple to use as the inks are applied by convenient pen, powder or spray applicators, and a portable ultra-violet light is provided for fluorescing the inks. The method is non-destructive as all of the ink compositions wash away upon normal cleaning.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A method for verifying cleaning services using an ultraviolet light and a contact marker for applying invisible fluorescent compound to an area subject to periodic cleaning, said method comprising the following steps:

marking an area subject to periodic cleaning with said invisible fluorescent compound using said contact marker;

inspecting said area subject to periodic cleaning by illumination with said ultraviolet light sometime after the marking process to determine whether said invisible fluorescent compound is still present;

whereby a determination that said invisible fluorescent compound is no longer present indicates that said area was properly cleaned sometime between said steps of marking and inspecting, or a determination that said invisible fluorescent compound is still present indicates that said area was not properly cleaned sometime between said steps of marking and inspecting.

2. The method for verifying cleaning services according to claim 1, further comprising the step of testing a surface to be cleaned and inspected to determine an appropriate fluorescent compound and applicator prior to said marking step.

* * * * *